US011443849B2

(12) United States Patent
Wegner (10) Patent No.: US 11,443,849 B2
(45) Date of Patent: Sep. 13, 2022

(54) CONCERTED ALARM HANDLING FOR A GROUP OF DIALYSIS APPARATUSES

(71) Applicant: Fresenius Medical Care Deutschland GmbH, Bad Homburg (DE)

(72) Inventor: Stefan Wegner, Werneck (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 436 days.

(21) Appl. No.: 16/461,215

(22) PCT Filed: Nov. 15, 2017

(86) PCT No.: PCT/EP2017/079257
§ 371 (c)(1),
(2) Date: May 15, 2019

(87) PCT Pub. No.: WO2018/091492
PCT Pub. Date: May 24, 2018

(65) Prior Publication Data
US 2019/0279766 A1    Sep. 12, 2019

(30) Foreign Application Priority Data
Nov. 16, 2016  (DE) .................. 102016121980.0

(51) Int. Cl.
*G16H 40/67*  (2018.01)
*G16H 40/20*  (2018.01)
*G16H 20/40*  (2018.01)

(52) U.S. Cl.
CPC ............. *G16H 40/67* (2018.01); *G16H 40/20* (2018.01); *A61M 2205/18* (2013.01); *A61M 2205/52* (2013.01); *G16H 20/40* (2018.01)

(58) Field of Classification Search
CPC ........ G16H 40/63; G16H 40/67; G16H 20/40; G16H 20/17; G16H 40/40; G16H 40/60; A61M 2205/18; A61M 1/14
See application file for complete search history.

(56) References Cited

U.S. PATENT DOCUMENTS

| 6,406,426 B1 | 6/2002 | Reuss et al. |
| 2002/0022894 A1 | 2/2002 | Eryurek et al. |

(Continued)

FOREIGN PATENT DOCUMENTS

| JP | H05-007623 | 1/1993 |
| JP | 2012-000291 | 1/2012 |

(Continued)

OTHER PUBLICATIONS

M. A. Estudillo-Valderrama et al., "A Distributed Approach to Alarm Management in Chronic Kidney Disease," in IEEE Journal of Biomedical and Health Informatics, vol. 18, No. 6, pp. 1796-1803, Nov. 2014, doi: 10.1109/JBHI.2014.2333880 (Year: 2014).*

(Continued)

*Primary Examiner* — Joseph D Burgess
(74) *Attorney, Agent, or Firm* — Fish & Richardson P.C.

(57) ABSTRACT

Concerted processing of a multiplicity of local apparatus status messages from dialysis apparatuses can be performed to enhance the quality of patient care delivered using the dialysis apparatuses. Typically, the dialysis apparatuses are operated in a group. A control agent, as described herein, performs a central calculation of prioritised warning messages for the group of dialysis apparatuses. The prioritisation is calculated in a concerted calculation according to a preconfigured system of rules.

18 Claims, 2 Drawing Sheets

(56) References Cited

U.S. PATENT DOCUMENTS

| | | | |
|---|---|---|---|
| 2005/0055242 A1* | 3/2005 | Bello | G16H 20/17 705/2 |
| 2005/0242928 A1 | 11/2005 | Kirkeby | |
| 2007/0213600 A1 | 9/2007 | John et al. | |
| 2007/0254593 A1 | 11/2007 | Jollota et al. | |
| 2011/0001605 A1* | 1/2011 | Kiani | G16H 30/20 340/5.6 |
| 2011/0107251 A1* | 5/2011 | Guaitoli | G16H 40/40 715/772 |
| 2013/0018355 A1* | 1/2013 | Brand | G16H 40/67 604/93.01 |
| 2013/0132977 A1* | 5/2013 | Doyle | G16H 40/63 719/318 |
| 2013/0191513 A1 | 7/2013 | Kamen et al. | |
| 2013/0310726 A1* | 11/2013 | Miller | G16H 20/17 604/5.04 |
| 2014/0028464 A1 | 1/2014 | Garibaldi | |
| 2014/0099235 A1 | 4/2014 | Ellingboe et al. | |
| 2016/0148496 A1 | 4/2016 | Bingley et al. | |
| 2016/0113595 A1 | 5/2016 | Meredith et al. | |

FOREIGN PATENT DOCUMENTS

| | | |
|---|---|---|
| JP | 2016-063464 | 4/2016 |
| JP | 2016-154780 | 9/2016 |
| WO | WO 2015/130674 | 9/2015 |

OTHER PUBLICATIONS

International Preliminary Report on Patentability in Application No. PCT/EP2017/079257, dated May 21, 2019, 6 pages.
International Search Report and Written Opinion in Application No. PCT/EP2017/079257, dated Feb. 27, 2018, 7 pages.

* cited by examiner

CONCERTED ALARM HANDLING FOR A GROUP OF DIALYSIS APPARATUSES

CROSS-REFERENCE TO RELATED APPLICATIONS

The present application is the national stage entry of International Patent Application No. PCT/EP2017/079257, filed on Nov. 15, 2017, and claims priority to Application No. DE 10 2016 121 980.0, filed in the Federal Republic of Germany on Nov. 16, 2016, the disclosures of which are expressly incorporated herein in entirety by reference thereto.

TECHNICAL FIELD

The present disclosure relates to the technical processing of alarm messages and warnings from dialysis apparatuses and relates in particular to a networked status message system, a control agent and to a method of controlling a group of dialysis apparatuses during handling of messages, in particular alarm messages.

BACKGROUND

Dialysis apparatuses are used in dialysis clinics in which, in general, several patients are treated at the same time. The qualified personnel are tasked with a large number of work steps and are responsible for ensuring the fault-free operation of a group of apparatuses. Under specific operating conditions, in exceptional situations or in the event of a fault, the dialysis apparatus automatically generates messages which represent the respective exceptional situation or the fault. These messages can be output in a visual and/or acoustic format. The messages can signal e.g. a fault condition on the apparatus. The messages are to be acknowledged by the user. If a fault message occurs, it is generally necessary to perform an action on the apparatus, in order to restore the apparatus to an operable state as rapidly as possible. If the message relates e.g. to the indication that blood loss in the extracorporeal blood circulation system has been detected, then this alarm message has a high priority in order that the cause of this fault can be found immediately and that the safety of the patient can continue to be ensured so that the apparatus can then be returned to a fault-free operating mode. Therefore, the user will initially confirm or acknowledge the message in order then to take appropriate measures. If the fault is successfully overcome, this is detected by the apparatus so that the message no longer appears.

In general, current, modern medical-technical apparatuses, such as the haemodialysis system 5008 from Fresenius Medical Care, can be equipped with a visual display device for outputting messages in relation to the status of the medical-technical apparatus. The display device can be operated in the manner of traffic lights and signals a fault-free operation e.g. by means of a green light signal and signals an alarm by means of a red light signal (e.g. in flashing mode). This signalling renders it possible for qualified personnel to be able to identify even from a remote position the condition of the apparatus and how urgently a message has to be dealt with.

In clinical practice, it is absolutely essential for the medical-technical apparatus to function in a fault-free manner. Therefore, in the case of the previous systems each medical-technical apparatus (e.g. dialysis apparatus) is designed having such a display device which is activated locally by the apparatus. As mentioned above, the dialysis apparatuses are used in practice generally in a dialysis department and thus as a group of apparatuses. By reason of the local activation of the display device, it is disadvantageously not possible in the case of existing apparatuses to differentiate from a distance which message is to be dealt with as a priority because a capability for differentiating between the different messages is not provided.

SUMMARY

Therefore, proceeding from the known systems as the prior art, the systems and methods described herein are intended to improve the handling of apparatus messages and to provide in particular a capability for differentiating between the status messages of the individual apparatuses of the group of apparatuses. Furthermore, it should be possible to prioritise all status messages for the apparatuses of the group in order to reduce the period of time for establishing a fault-free operating condition (by performing necessary measures). Furthermore, operation of the apparatus is to be improved with operation control in accordance with apparatus messages, which increases the quality of apparatus deployment.

In accordance with the systems and methods described herein, this object is achieved by means of a networked status message system, a control agent and methods disclosed herein.

The systems and methods are described herein with the aid of the solution involving a device, and therefore, inter alia, with the aid of the status message system. Features, advantages or alternative embodiments mentioned therein are likewise also to be transferred to the other claimed subjects and vice versa. In other words, the apparatus claims (which are directed e.g. to a control agent or a system) can also be developed with the features which are described or claimed in conjunction with the method and vice versa. In so doing, the corresponding functional features of the method are embodied by corresponding modules forming the apparatus, in particular by electronic hardware modules or microprocessor modules, of the system or of the device, and vice versa.

According to a first aspect, this disclosure relates to a networked status message system for a group of medical-technical apparatuses. The medical-technical apparatuses can be in particular dialysis apparatuses. The status message system comprises:

- a multiplicity of medical-technical apparatuses, wherein each medical-technical apparatus comprises a local signal device which is intended to detect a local apparatus status message or an apparatus condition. The local apparatus status message can comprise an apparatus fault message, a warning, an emergency signal and/or an alarm message.
- a control agent having an evaluation circuit which is intended for concerted calculation of prioritised warning messages for the group of medical-technical apparatuses on the basis of the detected, local apparatus status messages and for transmission of the calculated, prioritised warning messages to the local signal devices for the group of medical-technical apparatuses. In a preferred embodiment of the invention, the warning messages can be prioritised in a correlated manner, i.e. they have a relative prioritisation in relation to one another.
- a network for exchanging data between the medical-technical apparatuses and the control agent.

The concepts used in this disclosure are defined hereinunder.

The detected, local apparatus status messages relate to a condition of the medical-technical apparatus or of the technical devices (pumps, hose systems etc.) connected to the apparatus, and can be fault or alarm messages. The respective local apparatus status message can also comprise at least one sensor signal and/or other technical operating parameters of the medical-technical apparatus, from which the condition of the apparatus can be indirectly calculated.

The local signal device is implemented on each medical-technical apparatus and can comprise a visual and/or acoustic display device, e.g. in the form of traffic lights for displaying warning messages prioritised in a graded manner (green light for fault-free operation, flashing yellow light for a warning and red light or flashing red light for an alarm). In the prior art, the local signal device is only activated locally on the basis of locally detected signals of the respective medical-technical apparatus. According to the systems and methods described herein, the local signal device is activated in a concerted manner (e.g. centrally) via the control agent for all apparatuses of the group. Therefore, all of the local signal devices are activated in a concerted manner. Therefore, the condition of the other medical-technical apparatuses is taken into account during the activation. The local signal device can comprise a processor having an evaluation circuit. Furthermore, the local signal device is formed having an input interface and an output interface to the control agent. The local signal device serves to output a concerted warning message. In this context, the term "concerted" relates to the fact that the warning message has been calculated relatively in relation to the apparatus condition of all of the other apparatuses in the same time period. This can be performed at a central location. However, the concerted calculation can also be performed locally on a dedicated apparatus, but can still be performed in a centralised manner and jointly for all of the apparatuses of the group.

In one advantageous embodiment described herein, the local signal device can comprise a detection unit which is intended to detect the respective local apparatus status message of the apparatus or to detect an apparatus condition. The detection unit can be activated in predefined time intervals or after the occurrence of pre-definable events (e.g. in the event of a change in the condition of an apparatus of the group). An output unit of the local signal device then serves to output the (e.g. centrally) calculated prioritised warning message (and not the local apparatus status message detected locally on the apparatus, as was previously the case).

The evaluation circuit is an electronic component. It can be produced as hardware and/or software. The evaluation circuit can be designed e.g. as an electronic circuit which has digital and/or analogue circuit components and can comprise decision logic. The decision logic serves to decide which priority is to be allocated to a respective local apparatus status message in relation to the other apparatus status messages in the same time period or which apparatus status message is to acquire a higher priority and which is to acquire a subordinate priority in each case. For evaluation purposes, the evaluation circuit can access a system of rules which can be stored in particular in the form of rules in a database or in a memory and defines a protocol or a policy for prioritising a quantity of local apparatus status messages. The evaluation circuit can be activated automatically if a change in condition occurs in the group of medical-technical apparatuses, i.e. in at least one of the apparatuses, or even after other pre-configurable events or pre-configurable time intervals.

The evaluation circuit is preferably allocated to a specific medical-technical apparatus which functions as an administrator apparatus or as a control agent. The evaluation circuit can be provided centrally in the system or locally on all of the apparatuses and can exchange data with a central server which collects data from all or from selected ones of the medical-technical apparatuses (e.g. from all of the dialysis apparatuses of a dialysis station) and evaluates this data (e.g. by means of a statistical evaluation). It is also possible to design an evaluation circuit for a plurality of medical-technical apparatuses which can then trigger the messages from the apparatuses depending upon the identity of the apparatus (e.g. by means of a corresponding identification indication). The evaluation circuit serves to centrally evaluate all of the local apparatus status messages in a corresponding time period and serves to calculate prioritised warning messages.

The control agent is an electronic component and can be implemented on a computer or on a medical-technical apparatus or can be allocated thereto. In a first embodiment of the invention, the control agent functions as a central control apparatus for all medical-technical apparatuses of the group in order to calculate in a concerted manner for the entirety of the group apparatuses a prioritised list of warning messages on the basis of the detected local apparatus status messages. According to a second embodiment of the invention, the control agent functions in a decentralised manner and is installed on each of the medical-technical apparatuses. In this second embodiment of the invention, the control can be performed completely in a decentralised manner. This has the technical advantage that the use of additional hardware (server, master apparatus) is not required. For instance, the control agent can be implemented on all or selected ones of the medical-technical apparatuses. All of the (participating) medical-technical apparatuses then transmit and receive their respectively currently available status/operating conditions and each apparatus (machine) can decide by reason of a locally stored list and a system of rules whether the local (i.e. its own) reported status is the most urgent or whether the priority thereof is to be calculated in relation to all of the other (external) reported statuses. It can then correspondingly initiate the transmission of a prioritised warning message.

The inventive concepts will be described hereinunder in the context of a dialysis apparatus as an example of a medical-technical apparatus, e.g. of a haemodialysis apparatus or of a peritoneal dialysis apparatus. However, for the person skilled in the art it is evident that the concepts can likewise be applied or transferred to other medical computerised apparatuses or (fluid-management) machines or blood-treatment apparatuses which output apparatus messages or apparatus fault messages via a user interface.

In some embodiments, the local signal device of the respective medical-technical apparatus is controlled in a modified manner by means of the calculated, prioritised warning messages. The phrase "in a modified manner" relates to two aspects: On the one hand, the local signal device—in contrast to previously—is no longer controlled only on the basis of locally detected signals of the respective medical-technical apparatus, but instead is controlled on the basis of control signals which are calculated centrally or locally by the control agent and are transmitted to the local signal device. On the other hand, the control is performed dynamically in dependence upon the condition of the group of apparatuses comprising all of the medical-technical apparatuses.

In accordance with a further aspect, the object of the disclosure is achieved by means of a control agent for concerted calculation of prioritised warning messages for a group of medical-technical apparatuses, comprising:
- an input interface which is intended to detect local apparatus status messages from the medical-technical apparatuses of the group, and
- an evaluation circuit which is intended for evaluation of the detected, local apparatus status messages and for concerted calculation of prioritised warning messages for the group of medical-technical apparatuses and which is also configured to transmit the calculated, prioritised warning messages via an output interface to the medical-technical apparatuses of the group for the modified control of the respective medical-technical apparatus.

In some embodiments, the control agent is implemented on a medical-technical apparatus and/or on a central server. This has the technical advantage that no additional hardware has to be provided. It is also possible to endow a dedicated medical-technical apparatus with the function of the control agent.

In some embodiments, the input interface is intended to detect all of the local apparatus status messages from the medical-technical apparatuses of the group in a pre-configurable time interval.

According to a further aspect, some embodiments include the performance of a method for the coordinated control of a group of medical-technical apparatuses with regard to the output of messages, comprising method steps of:
- detecting local apparatus status messages from medical-technical apparatuses of the group
- collecting and consolidating all of the detected, local apparatus status messages
- evaluating all of the collected and consolidated, detected, local apparatus status messages in order to calculate in a concerted manner prioritised warning messages for all of the medical-technical apparatuses of the group
- transmitting the prioritised warning message calculated for the respective medical-technical apparatus to the respective medical-technical apparatus for the modified, coordinated control of the medical-technical apparatuses of the group on the basis of the transmitted, prioritised warning message.

In some embodiments, it is possible to configure to which apparatuses of the group the concertedly calculated, prioritised warning message is/are to be transmitted. For example, it is possible to implement a setting that the prioritised warning message is transmitted only to those apparatuses of the group, from which in each case a local apparatus status message has been detected. This has the advantage that apparatuses operated without any faults are not encumbered with unnecessary messages. However, it can also be desirable that a display is provided on all of the apparatuses of the group. Therefore, by looking at only one apparatus the user automatically also has all of the other apparatuses in view (or is informed of the status thereof). Equally, it is possible also to output on the apparatuses prioritised warning messages from other "external apparatuses". In particular, the prioritised warning messages can be output from other external apparatuses which have a higher priority, so that the user is able to immediately identify the need to take action on an external apparatus.

In some embodiments, an output mode is allocated to the respective (in each case calculated) prioritised warning message. The output mode can comprise in particular a visual, acoustic warning signal and/or a warning signal in another format, wherein the prioritised warning message is output on the local signal device corresponding to the respective output mode. The output mode can be output e.g. in a visual format on a monitor of the medical-technical apparatus, in particular on a touch-screen monitor. For allocation purposes, a policy (protocol, optionally with access to a system of rules) which is stored in a memory can be accessed, which can make provision e.g. that a prioritised warning message having the highest priority level must always be output with a red flashing signal and additionally with an acoustic output as the output mode, whereas a low-priority warning signal is only output in visual form. In an advantageous manner, the policy for allocating the output mode to the priority level of the warning signal message can also be changed during the operation of the system. Moreover, the change can advantageously be implemented uniformly for all of the apparatuses.

In some embodiments, the originally detected, local apparatus status message can be displayed on the apparatus in addition to the prioritised warning message. Therefore, it is possible to signal locally (on the apparatus) that the local apparatus status message had to be changed (upgraded or downgraded) by reason of the data relating to the condition of the other apparatuses of the group.

In some embodiments, selected, local apparatus status messages can be allocated a lock flag which denotes that the respective apparatus status message must not be downgraded when calculating the prioritised warning message. This can increase security for important messages, by ensuring that the priority thereof is not reduced.

In some embodiments, the prioritised warning messages are calculated by means of a correlative negotiation regarding the urgency of all of the detected, local apparatus status messages on the basis of a pre-configurable system of rules. The system of rules can be stored on the control agent or on another central memory location accessible via network access, or can also be stored locally. In an advantageous manner, the system of rules can also be changed during operation and can be adapted to the respective medical requirements (e.g. treatment of emergency patients).

In some embodiments, the modified, coordinated control of the apparatus group is not performed on the basis of the local apparatus status message, but instead is performed on the basis of the warning message which is prioritised in relation to all of the apparatus status messages.

In some embodiments, the modified, coordinated control of the medical-technical apparatus can be activated and deactivated. Alternatively or cumulatively, the modified, coordinated control can be triggered automatically after the occurrence of a pre-definable event. In pre-configurable special medical cases (e.g. the treatment of emergency patients), it is possible to switch over to the output of the local apparatus status message—i.e. to the previous uncoordinated method, without the control agent performing a prioritisation. This can be helpful in particular when the network connection is interrupted or defective or cannot provide the required transmission bandwidth. To this end, in a preferred embodiment of the invention provision is made that the network connection between the medical-technical apparatuses and/or the control agent is automatically examined and that a fault signal is generated in the event that a fault is detected or the connection quality is inadequate. In response to the fault signal, the operation is then switched over from the coordinated control to the conventional, local control. This can preferably be performed automatically. In this case, the pre-definable event is thus a defective or inadequate network connection (or interface) and is based upon an automatic examination of the network connection or the respective interfaces.

In some embodiments, all of the calculated, prioritised warning messages are stored in an itemised addressable manner for each medical-technical apparatus and/or are output on an output unit. This advantageously increases the transparency and the user obtains locally at "his" apparatus information regarding the current condition of the other apparatuses of the group.

According some embodiments of the methods described herein, the method comprises the steps of:
   detecting a user identity which is in each case specific for a user of the respective medical-technical apparatus and/or
   detecting a location of the user of the respective medical-technical apparatus,
   wherein, in order to calculate the prioritised warning message for the respective medical-technical apparatus the detected user identity and/or the detected location are calculated.

According to some embodiments, in the event that high-priority warning messages have been calculated for a plurality of medical-technical apparatuses, the method comprises the method step of:
   generating a request command and transmitting the same to pre-configured entities via pre-configured data transmission channels.

The request command can comprise a message which signals that additional personnel are required and must be requested from other stations. In one development, the request command can be relayed automatically to further entities for the provision of personnel.

In the event that warning messages which are highly prioritised for a plurality of medical-technical apparatuses have been calculated, a collision check unit can be accessed. The collision check unit is intended to resolve priority conflicts. To this end, according to the stored system of rules, further parameters can be requested (e.g. duration and/or type of the detected local status message), in order to grade the priority.

Also disclosed herein is a computer program product which is, or can be, loaded in a memory of a computer or of an electronic or medical-technical apparatus, with a computer program to carry out the method described in more detail above, when the computer program is executed on the computer or the electronic or medical-technical apparatus.

Also disclosed herein is a computer program for carrying out all method steps of the method described in more detail above when the computer program is executed on a computer or an electronic or medical-technical apparatus. It is thus also possible for the computer program to be stored on a medium which can be read by the computer or the electronic or medical-technical apparatus.

In the following detailed description of the figures, exemplified embodiments, which are not to be understood to be limiting, together with the features and further advantages thereof will be discussed with the aid of the drawings.

DETAILED DESCRIPTION OF THE FIGURES

The systems and methods disclosed herein will be explained hereinunder in more detail with the aid of exemplified embodiments with reference to the figures.

The inventive concepts disclosed herein relates to the coordinated control of a group V of medical-technical apparatuses, in particular dialysis apparatuses D, with regard to the output of messages. To this end, each dialysis apparatus D comprises a local signal device 10 which is intended to output messages relating to the condition of the apparatus. Since a plurality of dialysis apparatuses D are operated in one dialysis station, the apparatuses D are combined into a group V.

In practice, it is frequently the case that in one time phase a plurality of dialysis apparatuses D output messages because they are in a condition to be reported (e.g. a fault condition). In this case, the precautionary measures of the invention can ensure that the messages output in parallel are prioritised or weighted according to urgency in order to enable the user to deal with them more efficiently. The prioritisation specifies to the user an action or eradication plan and he knows the sequence in which he has to attend to the dialysis apparatuses. For instance, on the whole he is able to establish a fault-free overall condition for the apparatus group V more rapidly.

Figure 1:
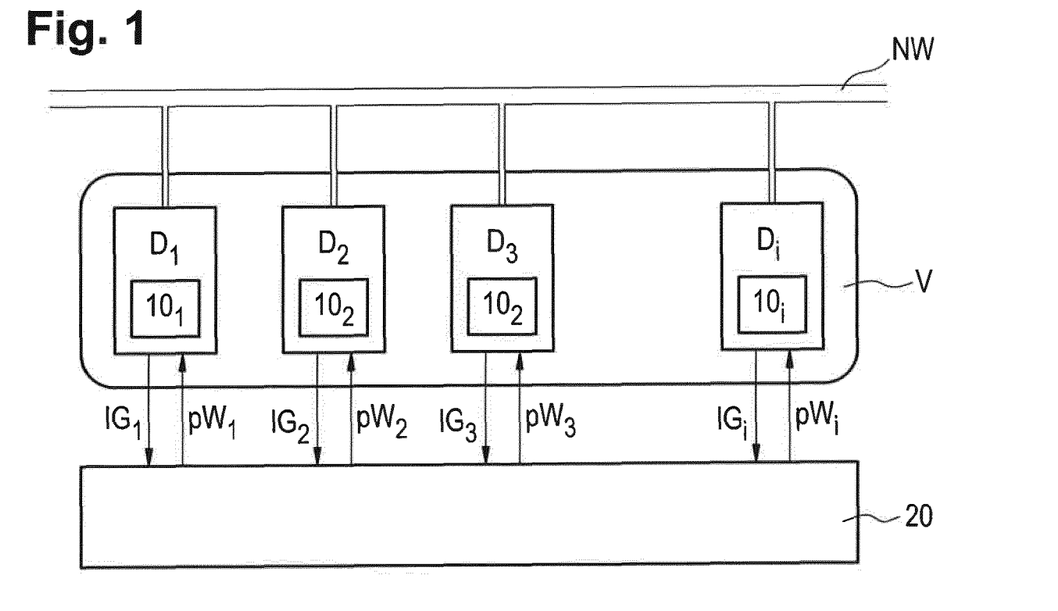
FIG. 1 shows a schematic view of a group of dialysis apparatuses exchanging data with a control agent according to one advantageous embodiment described herein.

As shown in FIG. 1, the group V in this example comprises the dialysis apparatuses $D_1$, $D_2$, $D_3$ and $D_1$ with their local signal devices 101, 102, 103, 101. The dialysis apparatuses D exchange data with a control agent 20 which is intended to process the local apparatus status messages lG in a coordinated manner. To this end, the locally detected local apparatus status messages lG are collected and evaluated and are prioritised according to a pre-configurable plan (policy). In particular, the urgency of the respective parallel messages in relation to one another is evaluated. To this end, the control agent can access the policy stored in a database DB. The calculated, prioritised warning messages pW are then transmitted as a message or message bundle to the respective dialysis apparatus D for local output at that location. The calculated, prioritised warning messages pW are preferably configured as an electronic data set.

The dialysis apparatuses D can exchange data with one another via a network NW. However, this is not absolutely necessary for the purpose of carrying out the invention and therefore is only optional.

Figure 2:
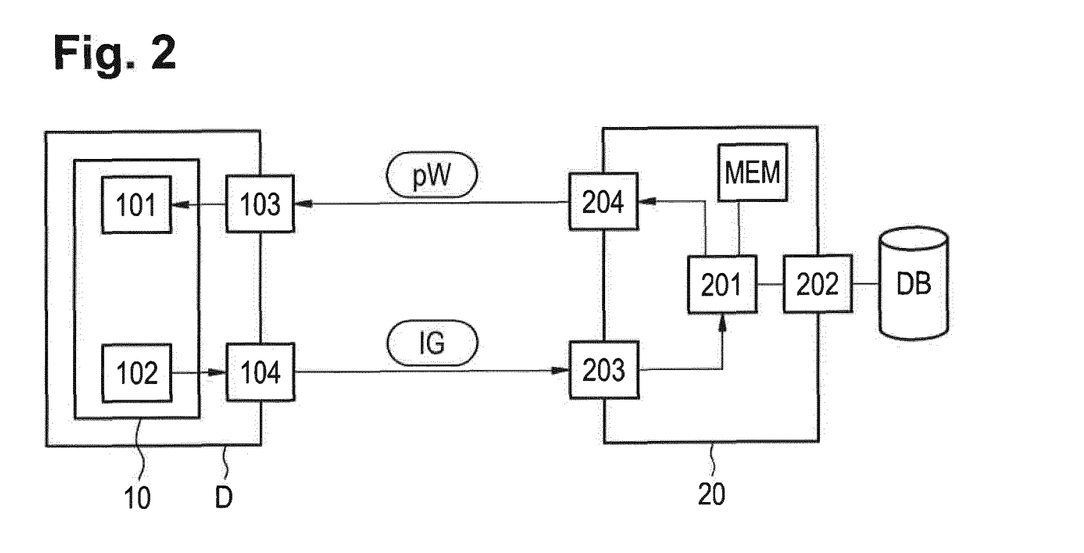
FIG. 2 shows further components of the local signal device and of the control agent and represents the exchange of data between the dialysis apparatus and the control agent.

FIG. 2 shows one of the dialysis apparatuses D of the group V and the control agent 20 with further components and the exchange of data between the apparatuses. The local signal device 10 typically comprises an output unit 101 which can be designed e.g. as a visual and/or acoustic output unit for outputting messages and in particular prioritised warning messages pW, and a detection unit 102 which is intended to detect the local apparatus status message lG. The local signal device 10 can have an input interface 103 and an output interface 104. The locally detected, local apparatus status message lG is transmitted to the control agent 20 via the output interface 104. The local signal device 10 receives the calculated, prioritised warning message pW from the control agent 20 via the input interface 103, in order to output said warning message to the output unit 101.

The control agent 20 comprises a detection interface 203, via which it receives the local apparatus status messages lG from the dialysis apparatuses D of the group V and which is in communication with an evaluation circuit by means of a processor 201. The processor 201 uses all of the consolidated local apparatus status messages lG from the dialysis apparatuses D of the group V to calculate a quantity of prioritised warning messages and in particular a prioritised warning message pW for each dialysis apparatus D which it transmits to the local signal device 10 via the signal output interface 204. In order to calculate in a concerted manner the prioritised warning messages pW for the apparatus group V, the processor 201 can use a database interface 202 to access a database DB, in which rules are stored as a policy for evaluating the local apparatus status messages lG.

The control agent 20 can comprise a memory MEM, in which allocations can be stored. For instance, for each dialysis apparatus D the prioritised warning message pW specifically calculated for it is stored with a specific priority. The priority represents the urgency of the respective local apparatus status message lG in the context of all of the other local apparatus status messages (of the other dialysis apparatuses D). In this case, the following allocation can be stored:

| | | |
|---|---|---|
| $D_1$ | $pW_1$ | Prio 1 |
| $D_2$ | $pW_2$ | Prio 3 |
| $D_3$ | $pW_3$ | Prio 1 |
| $D_4$ | $pW_4$ | Prio 2 |
| $D_5$ | $pW_5$ | Prio 3 |

If the apparatuses D are listed according to the urgency of their messages, the following sequence is produced in the above example: $D_1/D_3$-$D_4$-$D_2/D_5$. The apparatuses 1 and 3 and 2 and 5 each have the same priority. In the case of a correspondence in terms of priority, further parameters can be requested in order to be able to determine the respective apparatus condition in even greater detail and to be able to provide a further differentiation.

In addition, in the memory MEM an output mode can be allocated to the parameters listed in the above table. The output mode denotes the form in which the prioritised warning message pW is to be output on the local signal device 10. In this case, e.g. the duration of the message, the format (visual and/or acoustic), with or without flashing mode, the sound volume or brightness etc. can be adjusted. The output mode can be adjusted differently from apparatus to apparatus. It can also be preconfigured differently for each priority.

Figure 3:
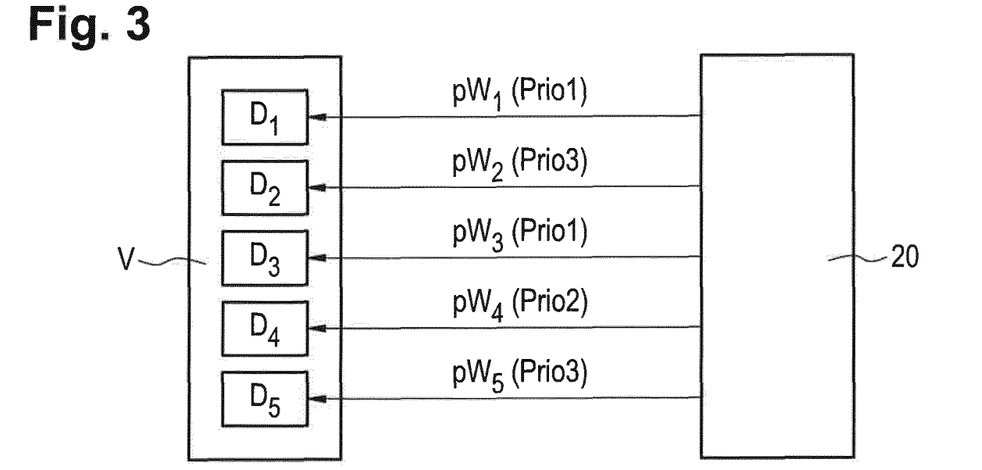
FIG. 3 schematically shows the exchange of data between the dialysis apparatus and the control agent according to a first embodiment described herein.

In a first embodiment, the system can be operated in a singular mode which is illustrated by way of example in FIG. 3. In the singular mode, only the one prioritised warning message pW which is calculated for the respective dialysis apparatus is transmitted to the dialysis apparatus D. The calculated, prioritised warning messages pW correspond to those of the example illustrated in the above table. Therefore, only the prioritised warning message $pW_1$ relating to the first apparatus is transmitted (with priority 1) to the first apparatus $D_1$, therefore only the prioritised warning message $pW_2$ relating to the second apparatus is transmitted (with priority 3) to the second apparatus $D_2$, . . . therefore only the prioritised warning message $pW_5$ relating to the fifth apparatus is transmitted (with priority 3) to the fifth apparatus $D_5$. If the system is operated in this singular mode, the data volume transmitting between the apparatuses D and the control agent 20 can be reduced.

Figure 4:
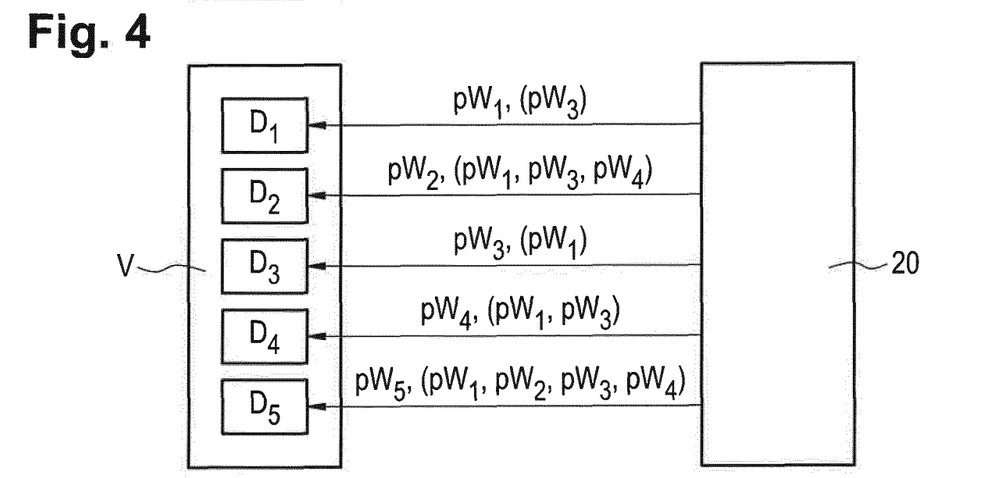
FIG. 4 shows the exchange of data according to a second embodiment described herein.

FIG. 4 shows a second embodiment, in which the system is operated in a group mode. In the group mode, not only the prioritised warning message pW relating to the respective dialysis apparatus D is transmitted by the control agent 20 to the dialysis apparatus D, but also all or selected ones of the external, prioritised warning messages pW for external apparatuses (i.e. external, other dialysis apparatuses D of the group V) are transmitted to the respective dialysis apparatus D. In some embodiments, only the prioritised warning messages having the same or higher priority are transmitted. Although this requires a higher data volume which must be transmitted by the control agent 20 to the local signal device, it permits locally at the respective dialysis apparatus D more information regarding the overall situation of the group V. For instance, a user working at a second dialysis apparatus $D_2$ on which the prioritised warning message $pW_2$ is output with priority 3 (relatively low urgency) can be informed regarding the fact that a maximum-priority warning message is output with priority 1 on the first and third dialysis apparatuses $D_1$, $D_3$. This enables the user to verify whether he can briefly change work station in order to process the message on the first or third apparatus. Accordingly, the user at the fifth dialysis apparatus $D_5$ is informed that on the external, fourth dialysis apparatus $D_4$, to which the fourth prioritised warning message $pW_4$ is allocated, the priority thereof is 2. It is obvious to the person skilled in the art that it is possible not to transmit the external prioritised warning messages pW (which are intended for other apparatuses and have the same or higher priority), but to transmit only an indication to the respective dialysis apparatus D to which the message pW is allocated.

In one advantageous development of the systems and methods described herein, in addition to being able to display the priority signals from external apparatuses D of the group V it is also possible to display the position thereof on a graphics card, so that the user is directly informed about where the apparatuses D with the respective high-priority warning message are located. This development can be used advantageously in the group mode.

Figure 5:
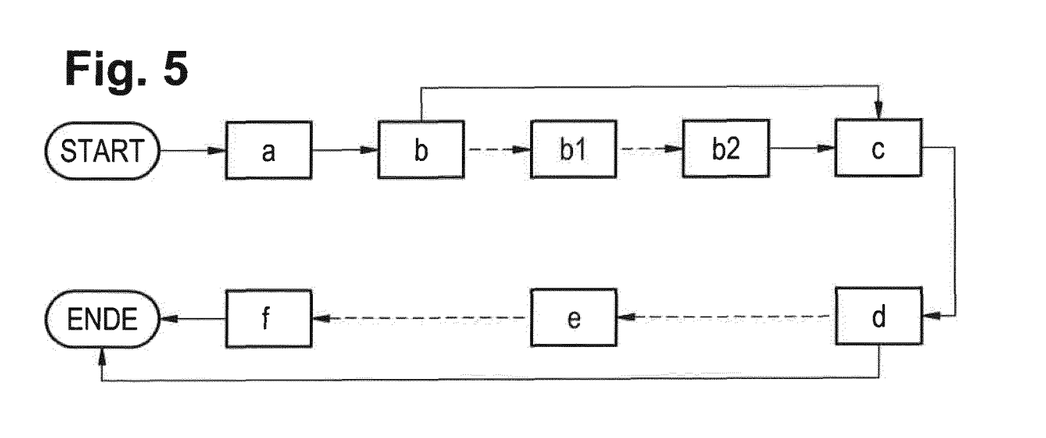
FIG. 5 is a flow diagram of a method according to some embodiments described herein.

FIG. 5 shows a flow diagram of the method according to one exemplified embodiment. After the start of the method, in step a, the local apparatus status messages lG are detected on all or selected ones of the apparatuses of the group V. In step b, the detected, local apparatus status messages lG are collected and consolidated in a coordinated manner, preferably on the control agent 20. Then, in step c the consolidated, local apparatus status messages lG are evaluated—preferably but not necessarily centrally—in order to generate a quantity of prioritised warning messages pW, in which the overall condition of all of the apparatuses of the group is calculated and taken into account. In step d, the calculated, prioritised warning messages pW can be transmitted to the dialysis apparatuses D for output.

As illustrated by the dotted arrows in FIG. 5, in one possible development of the invention step b is followed by step b1, in which a user identity of the user of the dialysis apparatus D is detected. It is also possible to detect a location of the user in step b2. Depending upon which parameters have been detected, these are taken into account when calculating the prioritised warning message pW.

In one advantageous embodiment, in step e an output mode can be allocated to each prioritised warning message pW. The output mode denotes the type of output on the local signal device 10. The output mode can denote a visual, acoustic and/or other-format output of a warning signal, wherein the prioritised warning message pW is output on the local signal device 10 or on an output unit of the dialysis apparatus (e.g. a monitor).

In a further embodiment, in step f a request command can be generated. The request command can signal e.g. that further qualified personnel are required to process the prioritised warning messages pW output in parallel. The request commands can be requested by the qualified personnel e.g. directly from the detected location. In so doing, it is possible to take into account the qualification of the qualified personnel, in order to book e.g. more highly qualified personnel for high-priority warning messages. The location can be determined e.g. by work plans and/or time recording systems. Alternatively, for locating purposes it is possible to use pagers which the person carries around with him and of which the signals are detected. The request command can be relayed to further computer-based entities (e.g. external dialysis apparatuses D or to pagers which the qualified personnel carry around with them) or by means of other message formats, such as e-mail or SMS) in order to signal at a remote location that there is a need to take action.

Finally, it is noted that the description of the invention and the exemplified embodiments are fundamentally to be understood to be non-limiting with respect to a specific physical implementation of the invention. All features explained and illustrated in conjunction with individual embodiments of the invention can be provided in different combinations in the subject matter in accordance with the invention in order to achieve the advantageous effects thereof at the same time. Therefore, it is thus e.g. likewise within the scope of the invention, as an alternative or in addition to the output unit of the local signal device, to provide other output units e.g. the graphical user interface of the medical apparatus, on which the prioritised warning message pW is output. For a person skilled in the art, it is particularly obvious that the invention can be used not just for dialysis apparatuses but also for other medical-technical apparatuses D, in which an apparatus status is to be monitored and which are operated in a group V of apparatuses. The messages can be fault messages but can also be other messages in relation to a condition of an apparatus.

Furthermore, the components of the medical system for coordinated message handling or for fault handling can be distributed over a plurality of physical products.

The scope of protection of the present invention is set by the claims and is not limited by the features explained in the description or shown in the figures.

REFERENCE SIGNS

D medical-technical apparatus, in particular a dialysis apparatus
V group of medical-technical apparatuses
10 local signal device
101 output unit
102 detection unit for local apparatus status message
103 input interface
104 output interface
20 control agent
201 microprocessor with evaluation circuit
202 database interface
203 detection interface
204 signal output interface
DB database
NW network
lG local apparatus status message
pW prioritised warning message
a detecting the local apparatus status message
b collecting and consolidating the detected, local apparatus status messages
b1 detecting a user identity
b2 detecting a location
c evaluating the collected, local apparatus status messages
d transmitting the prioritised warning messages to the medical-technical apparatuses
e allocating an output mode
f generating a request command

The invention claimed is:

1. A networked status message system for a group of dialysis apparatuses, the system comprising:
the group of dialysis apparatuses, wherein each dialysis apparatus comprises a local signal device configured to detect local dialysis apparatus status messages and to transmit the local dialysis apparatus status messages to a control agent; and
the control agent configured to receive the local dialysis apparatus status messages and comprising an evaluation circuit, the evaluation circuit configured for: (i) accessing a system of rules and (ii) prioritizing the local dialysis apparatus status messages based on the system of rules to calculate prioritised warning messages for the group of dialysis apparatuses on the basis of the detected, local apparatus status messages,
wherein the control agent is configured to transmit the calculated, prioritised warning messages to: (i) only the local signal devices of the group of dialysis apparatuses that transmitted one or more of the local dialysis apparatus status messages to the control agent and (ii) none of the local signal devices of the group of dialysis apparatuses that did not transmit one or more of the local dialysis apparatus status messages to the control agent, and
wherein each of the local signal devices is configured to receive and display one or more of the calculated, prioritised warning messages.

2. The system of claim 1, wherein the local signal devices of respective dialysis apparatuses are configured to be controlled in a modified manner based on the calculated, prioritised warning messages.

3. A control agent system for calculating prioritised warning messages for a group of dialysis apparatuses, the control agent system comprising:
an input interface configured to receive local apparatus status messages from the group of dialysis apparatuses; and
an evaluator configured to access a system of rules and for evaluation of the received local apparatus status messages based on the system of rules to calculate prioritised warning messages for the group of dialysis apparatuses,
wherein the evaluator is also configured to transmit the calculated prioritised warning messages via an output interface to: (i) each dialysis apparatus of the group of dialysis apparatuses from which one or more of the local apparatus status messages were received by the control agent and (ii) no dialysis apparatuses of the group of dialysis apparatuses from which none of the local apparatus status messages were received by the control agent, and wherein the prioritised warning messages are transmitted for display only by each dialysis apparatus from which one or more of the local apparatus status messages were received by the control agent and for control thereof based on the prioritised warning messages.

4. The control agent system of claim 3, wherein the control agent is implemented on a medical-technical apparatus or on a central server.

5. The control agent system of claim 3, wherein the input interface is configured to detect all local apparatus status messages from each dialysis apparatus of the group of dialysis apparatuses in a pre-configurable time interval or after an occurrence of a configurable event.

6. A method for coordinated control of a group of dialysis apparatuses, the method comprising:
   detecting local apparatus status messages from one or more dialysis apparatuses of the group of dialysis apparatuses;
   collecting and consolidating all of the detected, local apparatus status messages over a period of time;
   evaluating all of the collected and consolidated, detected, local apparatus status messages in order to calculate, in a concerted manner and using a system or rules, prioritised warning messages for the one or more dialysis apparatuses of the group of dialysis apparatuses that detected at least one of the local apparatus status messages; and
   transmitting the prioritised warning messages to: (i) the one or more dialysis apparatuses of the group of dialysis apparatuses that detected at least one of the local apparatus status messages and (ii) none of the dialysis apparatuses of the group of dialysis apparatus that did not detect a local apparatus status message,
   wherein the prioritised warning messages are transmitted for display only by the one or more dialysis apparatuses of the group of dialysis apparatus that detected at least one of the local apparatus status messages and for coordinated control thereof on the basis of the transmitted, prioritised warning messages.

7. The method of claim 6, wherein the evaluation is performed in a coordinated manner for all dialysis apparatuses of the group of dialysis apparatuses and the evaluation is performed centrally or locally on each dialysis apparatus of the group of dialysis apparatuses.

8. The method of claim 6, wherein for each of the prioritised warning messages an output mode is calculated and allocated, wherein the output mode comprises output of a visual warning signal, an acoustic warning signal, or a warning signal in another format, so that the prioritised warning message is output on a local signal device or on an output unit in the output mode.

9. The method of claim 6, wherein the local apparatus status message is output in addition to the prioritised warning messages in order to represent a change in the local apparatus status message.

10. The method of claim 6, wherein selected local apparatus status messages can be allocated a lock flag which denotes that the selected apparatus status messages must not be downgraded by the calculated, prioritised warning message.

11. The method of claim 6, wherein the prioritised warning messages are calculated using a correlative negotiation regarding an urgency of all of the detected, local apparatus status messages using a pre-configurable system of rules.

12. The method of claim 6, wherein the modified, coordinated control is not performed based on the local apparatus status message, but instead is performed based on the warning message which is prioritised in relation to all of the local apparatus status messages.

13. The method of claim 6, wherein the modified, coordinated control of the group of dialysis apparatuses can be activated and deactivated or is triggered automatically after an occurrence of a pre-defined event.

14. The method of claim 6, wherein all of the calculated, prioritised warning messages are output in an itemized addressable manner for each dialysis apparatus of the group of dialysis apparatuses.

15. The method of claim 6, wherein all of the calculated, prioritised warning messages are stored in an itemized addressable manner for each dialysis apparatus of the group of dialysis apparatuses.

16. The method of claim 6, further comprising:
   detecting a user identity which is in each case specific for a user of a respective dialysis apparatus of the group of dialysis apparatuses; and
   detecting a location of the user of the respective dialysis apparatus,
   wherein, in order to calculate the prioritised warning message for the respective dialysis apparatus the detected user identity and the detected location are calculated.

17. The method of claim 6, further comprising: (i) detecting a user identity which is in each case specific for a user of a respective dialysis apparatus of the group of dialysis apparatuses, or (ii) detecting a location of a user of a respective dialysis apparatus, wherein, in order to calculate the prioritised warning message for the respective dialysis apparatus the detected user identity or the detected location are calculated.

18. The method of claim 6, wherein, when high-priority warning messages have been calculated for a plurality of dialysis apparatuses of the group of dialysis apparatuses, the method further comprises:
   generating a request command and transmitting the request command to pre-configured entities via pre-configured data transmission channels.

* * * * *